(12) United States Patent
Wogoman et al.

(10) Patent No.: US 11,426,179 B2
(45) Date of Patent: Aug. 30, 2022

(54) ORTHOPAEDIC SURGICAL INSTRUMENT SYSTEM AND METHOD INCLUDING A STEM TRIAL COMPONENT

(71) Applicant: DePuy Ireland Unlimited Company, Ringaskiddy (IE)

(72) Inventors: Thomas E. Wogoman, Warsaw, IN (US); Daniel E. Lashure, Warsaw, IN (US); Nathan C. Reeder, Warsaw, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 354 days.

(21) Appl. No.: 16/806,138

(22) Filed: Mar. 2, 2020

(65) Prior Publication Data

US 2020/0197026 A1     Jun. 25, 2020

Related U.S. Application Data

(62) Division of application No. 15/858,037, filed on Dec. 29, 2017, now Pat. No. 10,575,861.

(51) Int. Cl.
*A61B 17/16* (2006.01)
*A61F 2/46* (2006.01)
*A61B 17/00* (2006.01)

(52) U.S. Cl.
CPC ........ *A61B 17/1617* (2013.01); *A61B 17/164* (2013.01); *A61B 17/1633* (2013.01); *A61B 17/1675* (2013.01); *A61F 2/4684* (2013.01); *A61B 2017/00526* (2013.01)

(58) Field of Classification Search
CPC ... A61B 17/16; A61B 17/1617; A61B 17/164; A61B 17/1633; A61B 17/1675; A61F 2/46; A61F 2/4684
See application file for complete search history.

(56) References Cited

U.S. PATENT DOCUMENTS

| 6,206,884 B1 | 3/2001 | Masini |
| 10,575,861 B2 | 3/2020 | Wogoman et al. |
| 2008/0039950 A1 | 2/2008 | Splieth et al. |

FOREIGN PATENT DOCUMENTS

| EP | 2786715 A2 | 10/2014 |
| EP | 2837365 A2 | 2/2015 |

OTHER PUBLICATIONS

Extended European Search Report for Application No. 18213378.5, dated Jun. 6, 2019, 7 pages.

*Primary Examiner* — Christopher J Beccia
(74) *Attorney, Agent, or Firm* — Barnes & Thornburg LLP

(57) ABSTRACT

A method of assembling an orthopaedic surgical instrument may include selecting a surgical reamer for use in resecting a portion of a patient's bone. The method may also include aligning an outer sleeve of a stem trial component with a distal end of a shaft of the surgical reamer. The method may also include advancing the outer sleeve into engagement with the distal end of the reamer shaft. The method may also include advancing a central rod of the stem trial component along a passageway defined in the outer sleeve into engagement with the distal end of the reamer shaft. The method may also include threading the central rod into the distal end of the reamer shaft to couple the stem trial component to the surgical reamer for use in resecting the portion of the patient's bone.

4 Claims, 7 Drawing Sheets

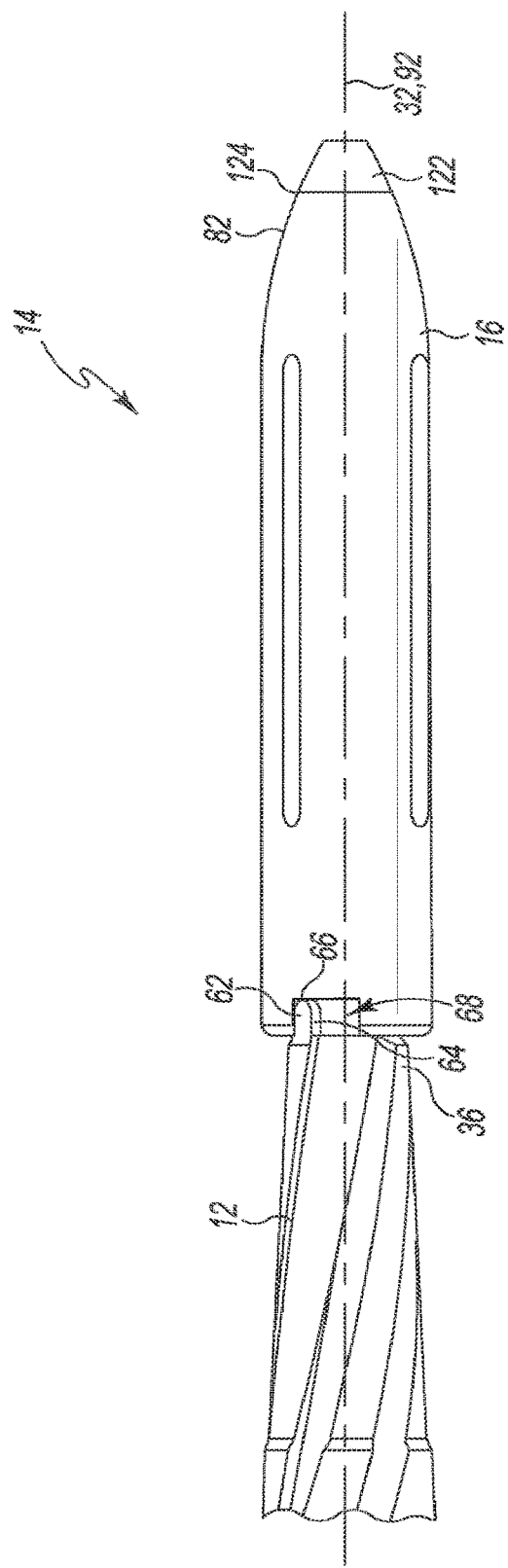
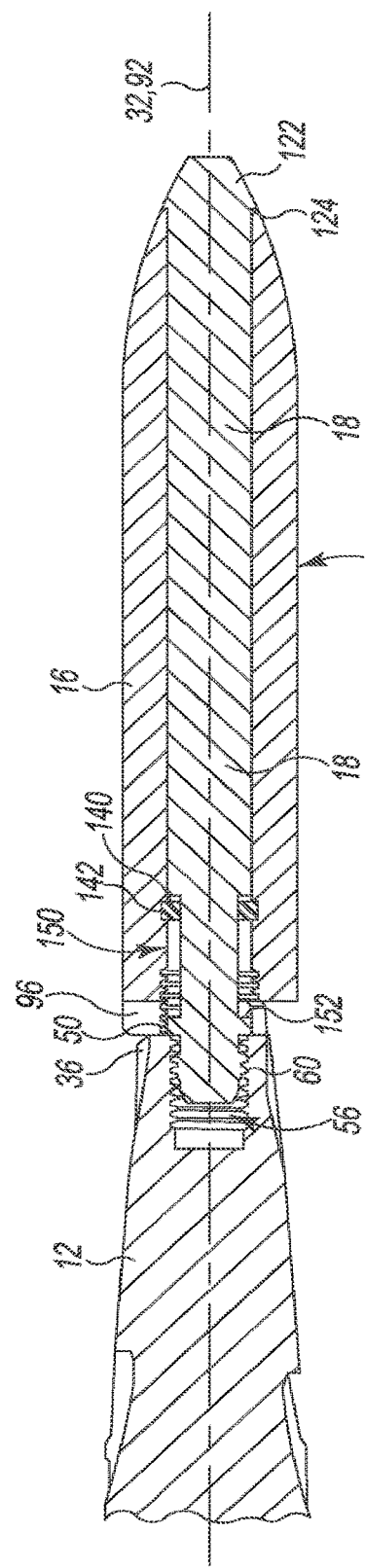

ORTHOPAEDIC SURGICAL INSTRUMENT SYSTEM AND METHOD INCLUDING A STEM TRIAL COMPONENT

This application is a divisional of U.S. patent application Ser. No. 15/858,037, now U.S. Pat. No. 10,575,861, filed Dec. 29, 2017, which is hereby incorporated by reference.

TECHNICAL FIELD

The present disclosure relates generally to orthopaedic instruments for use in the performance of an orthopaedic joint replacement procedure, and, more particularly, to orthopaedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes multiple prosthetic components, including a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur. An elongated stem component may be attached to the tibial tray or the femoral component to better secure the prosthesis to the patient's bone.

During any knee surgery, the orthopaedic surgeon typically uses a variety of different orthopaedic surgical instruments such as, for example, cutting blocks, reamers, drill guides, trial components, and other surgical instruments to prepare the patient's bones to receive the knee prosthesis.

SUMMARY

According to one aspect of the disclosure, an orthopaedic surgical instrument system comprising a modular stem trial component is disclosed. The modular stem trial component includes an outer sleeve and a central rod that is configured to be coupled to a surgical reamer to secure the modular stem trial component to the reamer. In some embodiments, the stem trial component may include a secondary retention mechanism to constrain relative rotation between the outer sleeve and the surgical reamer. The secondary retention mechanism may include a tab extending from one of the outer sleeve and the surgical reamer, and a slot that is sized to receive the tab that is defined in the other of the outer sleeve and the surgical reamer. The tab may include more than one tab, and the slot may include multiple slots that are sized to receive the tabs.

According to another aspect, the orthopaedic surgical instrument system comprises a surgical reamer including a shaft that extends to a distal end, a plurality of cutting flutes formed on the shaft, and a threaded aperture that is defined in the distal end of the shaft. The system also comprises a stem trial component that comprises an outer sleeve including a proximal end, a distal end, and a passageway extending from an opening defined in the proximal end to an opening defined in the distal end. The stem trial component also comprises a central rod including an elongated body positioned in the passageway of the outer sleeve, a threaded end positioned adjacent to the proximal end of the outer sleeve, a distal tip positioned adjacent to the distal end of the outer sleeve, and an annular shoulder wall defined between the elongated body and distal tip that engages a rim wall surrounding the opening defined in the distal end of the outer sleeve. The threaded end of the central rod is configured to be received in the threaded aperture of the surgical reamer to couple the stem trial component to the surgical reamer.

In some embodiments, the system may include a secondary retention mechanism to constrain relative rotation between the outer sleeve and the surgical reamer. In some embodiments, the secondary retention mechanism may include one of a tab and a slot on the distal end of the shaft of the surgical reamer. The outer sleeve of the stem trial component may include the other of a tab and a slot on the proximal end. The slot may be sized and shaped to receive the tab to constrain relative rotational movement between the outer sleeve and the surgical reamer.

Additionally, in some embodiments, the tab may be one of a plurality of tabs, and the slot may be one of a plurality of slots. Each slot may be defined between a pair of lobes. Each slot may be sized and shaped to receive one of the plurality of tabs to constrain relative rotational movement between the outer sleeve and the surgical reamer.

In some embodiments, the surgical reamer may include a distal tab that extends outwardly from the distal end of the shaft, the outer sleeve of the stem trial component may include an outer surface that extends from the proximal end and a slot that is defined in the proximal end. The slot may extend through the outer surface and open into the passageway. The slot may be sized and shaped to receive the distal tab of the surgical reamer to constrain relative rotational movement between the outer sleeve and the surgical reamer.

Additionally, in some embodiments, the distal tab of the surgical reamer may be a first distal tab of a plurality of distal tabs extending outwardly from the distal end of the shaft, and the slot may be a first slot of a plurality of slots defined in the proximal end of the outer sleeve. Each slot may be sized and shaped to receive one of the plurality of distal tabs of the surgical reamer to constrain relative rotational movement between the outer sleeve and the surgical reamer.

In some embodiments, the central rod may be configured to be rotated within the passageway of the outer sleeve of the stem trial component to permit the threaded end of the central rod to be threaded into the aperture of the surgical reamer when the tab is received in the slot.

In some embodiments, the passageway of the outer sleeve may extend along a longitudinal axis, and the central rod may be configured to slide along the longitudinal axis to advance the annular shoulder wall into and out of engagement with the rim wall surrounding the opening defined in the distal end of the outer sleeve.

In some embodiments, the central rod may be removably coupled to the outer sleeve of the stem trial component. In some embodiments, the stem trial component may include a retainer to secure the central rod to the outer sleeve.

In some embodiments, the retainer may be positioned in, and extend outwardly from, an inner groove that is defined in the outer sleeve. The elongated body of the central rod may include a pocket that receives the retainer to limit the movement of the central rod along the longitudinal axis.

In some embodiments, the distal tip of the central rod may include a frustoconical surface that extends from the annular shoulder wall to a substantially planar distal surface. Additionally, in some embodiments, the central rod may have a socket defined in the substantially planar distal surface.

In some embodiments, the outer sleeve may be formed from a polymer material. In some embodiments, the outer sleeve may be formed from a metallic material.

In some embodiments, the outer sleeve may be configured to be clamped between the annular shoulder wall of the central rod and the distal end of the shaft of the surgical reamer to secure the stem trial component to the surgical reamer.

According to another aspect, an orthopaedic surgical instrument is disclosed. The orthopaedic surgical instrument comprises a stem trial component, and the stem trial component comprises an outer sleeve including a proximal end, a distal end, and a passageway extending from an opening defined in the proximal end to an opening defined in the distal end. The stem trial component also comprises a central rod including an elongated body positioned in the passageway of the outer sleeve, a threaded end positioned adjacent to the proximal end of the outer sleeve, a distal tip positioned adjacent to the distal end of the outer sleeve, and an annular shoulder wall defined between the elongated body and distal tip that is configured to engage a rim wall surrounding the opening defined in the distal end of the outer sleeve.

The passageway of the outer sleeve extends along a longitudinal axis, and the central rod is configured to slide along the longitudinal axis to advance the annular shoulder wall into and out of engagement with the rim wall. The threaded end of the central rod is configured to be received in a threaded aperture of a surgical reamer to couple the stem trial component to the surgical reamer.

In some embodiments, the central rod may be removably coupled to the outer sleeve of the stem trial component. In some embodiments, the stem trial component may include a retainer to secure the central rod to the outer sleeve.

In some embodiments, the retainer may be positioned in, and extend outwardly from, an inner groove that is defined in the outer sleeve. In some embodiments, the elongated body of the central rod may include a pocket that receives the retainer to limit the movement of the central rod along the longitudinal axis.

In some embodiments, the outer sleeve of the stem trial component may include at least one of a slot and tab that is configured to engage the surgical reamer to constrain relative rotational movement between the outer sleeve and the surgical reamer.

According to another aspect, a method of assembling an orthopaedic surgical instrument is disclosed. The method comprises selecting a surgical reamer for use in resecting a portion of a patient's bone, aligning an outer sleeve of a stem trial component with a distal end of a shaft of the surgical reamer, advancing the outer sleeve into engagement with the distal end of the reamer shaft, advancing a central rod of the stem trial component along a passageway defined in the outer sleeve into engagement with the distal end of the reamer shaft, and threading the central rod into the distal end of the reamer shaft to couple the stem trial component to the surgical reamer for use in resecting the portion of the patient's bone.

In some embodiments, advancing the outer sleeve into engagement with the distal end of the reamer shaft may comprise positioning a distal tab extending from the distal end of the reamer shaft into a slot defined in the outer sleeve to constrain relative rotational movement between the outer sleeve and the surgical reamer.

In some embodiments, threading the central rod into the distal end of the reamer shaft may include threading the central rod into the distal end of the reamer shaft while the distal tab of the surgical reamer is received in the slot defined in the outer sleeve of the stem trial component.

In some embodiments, threading the central rod into the distal end of the reamer shaft may include clamping the outer sleeve between an annular shoulder wall of the central rod and the distal end of the shaft of the surgical reamer to prevent relative rotational movement between the stem trial component and the surgical reamer.

BRIEF DESCRIPTION OF THE DRAWINGS

The detailed description particularly refers to the following figures, in which:

FIG. 3 is a side elevation view of the system of FIG. 1;

FIG. 4 is a cross-sectional side elevation view taken along the axis 32 in FIG. 3;

DETAILED DESCRIPTION OF THE DRAWINGS

Figure 1:
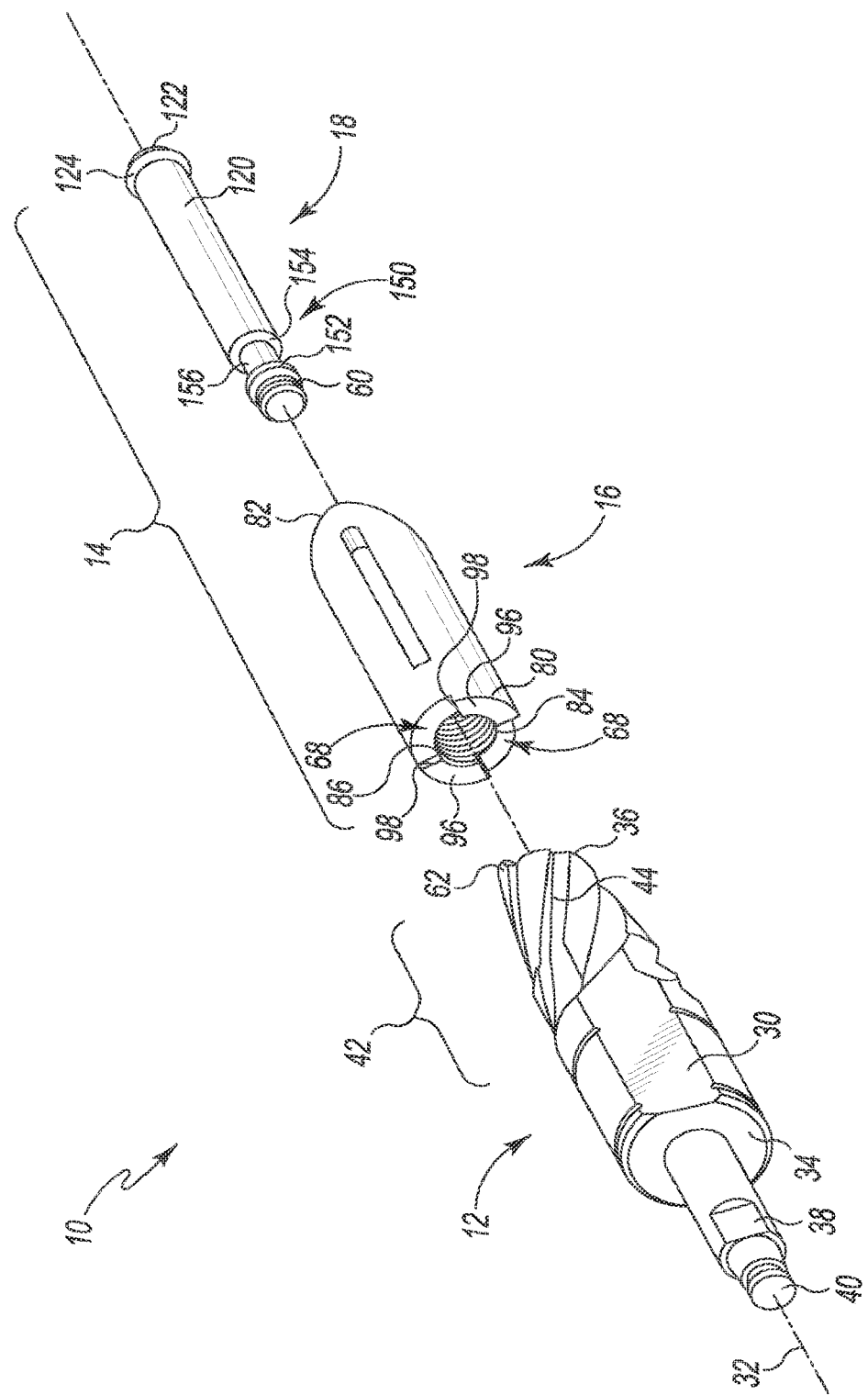
FIG. 1 is an exploded perspective view of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument system 10 is shown. The system 10 includes a surgical reamer 12 configured to be coupled to a surgical drill or other rotary tool and a stem trial component 14 configured to be coupled to the surgical reamer 12 for use during a surgical procedure. A person of ordinary skill would understand that the term "reamer" refers to a type of rotary cutting tool and the term "stem trial component" refers to a prosthetic trial component configured for use in sizing and selecting the prosthetic elongated stem component. Such stem trial components are shaped to match the size and shape as their corresponding elongated stem components but are not configured to be permanently implanted into the patient's bones. Instead, the stem trial component may be temporarily attached during surgery to the patient's bones to guide the reaming operation or in place of the prosthetic components to evaluate fit, range of motion, and other aspects of the patient's joint and assist the surgeon in selecting the prosthetic components of the orthopaedic prosthesis for implantation. The stem trial component 14 is therefore also configured to be secured to, for example, tibial tray trial components or femoral trial components. In the illustrative embodiment, the stem trial component 14 is a modular assembly including an outer sleeve 16 that defines the proximal portion of the trial geometry and an central rod 18 that extends through the outer sleeve 16 for attachment to the surgical reamer 12, as described in greater detail below.

The surgical reamer 12 includes a shaft 30 that extends along a longitudinal axis 32 from a proximal end 34 to a distal end 36. A shank 38 extends outwardly from the proximal end 34 of the shaft 30 and includes a mounting end 40 configured to engage the surgical drill (not shown) to secure the reamer 12 to the surgical drill. The reamer 12 also includes a plurality of cutting flutes 42 formed on the distal end 36 of the shaft 30. Each cutting flute 42 includes a cutting edge 44 configured to engage and remove material from a patient's bone. In the illustrative embodiment, the surgical reamer 12 is formed as a single monolithic component from a metallic material such as, for example, stainless steel, which may be autoclaved between surgical procedures. It should be appreciated that in other embodiments part of the reamer may be formed from a polymer or plastic material. In such embodiments, the cutting edges of the cutting flutes may be formed by a metallic coating or insert on the plastic.

As shown in FIG. 3, the distal end 36 of the reamer shaft 30 includes an annular rim wall 50 that surrounds an opening 52. An inner wall 54 extends inwardly from the opening 52 to define an aperture 56 in the distal end 36 of the shaft 30. A plurality of threads 58, which are configured to engage a corresponding threaded end 60 of the stem trial component 14, are formed on the inner wall 54.

In the illustrative embodiment, the surgical reamer 12 also includes a number of distal tabs 62 that extend outwardly from the rim wall 50 of the reamer shaft 30. Each distal tab 62 includes a pair of opposing side surfaces 64 that extend from the rim wall 50 to a tip 66. As described in greater detail below, the tabs 62 are sized to be received in corresponding slots 68 defined in the outer sleeve 16 of the stem trial component 14 to constrain the relative rotation between the outer sleeve and the reamer. The tabs 62 and the slots 68 together define a secondary retention mechanism of the system 10.

Returning to FIG. 1, the outer sleeve 16 has a proximal end 80 configured to engage the distal end 36 of the surgical reamer 12 and a distal end 82 positioned opposite the proximal end 80. An opening 84 is defined in the proximal end 80, and an inner wall 86 extends inwardly from the opening 84 to another opening 88 (see FIG. 2) defined in the distal end 82. The wall 86 and the openings 84, 88 cooperate to define a passageway 90 extending along a longitudinal axis 92 through the outer sleeve 16. In the illustrative embodiment, the inner wall 86 includes a plurality of threads 94 that are configured to engage a threaded end of another surgical instrument such as, for example, a removal tool that may be used to pull the stem trial component 14 from the canal in the unlikely event it became separated from the reamer or another trial component.

As described above, the outer sleeve 16 includes a pair of slots 68 that are sized to receive the distal tabs 62 of the surgical reamer 12. In the illustrative embodiment, the proximal end 80 of the outer sleeve 16 includes a pair of lobes 96 that are spaced apart around the outer circumference of the opening 84, and the slots 68 are defined by the lobes 96. As shown in FIG. 1, each lobe 96 includes angled side walls 98 that cooperate to define the slots 68. If the threaded connection between the surgical reamer 12 and the stem component 14 loosens during a surgical procedure, the distal tabs 62 of the surgical reamer 12 may be advanced by the rotation of the reamer 12 relative to the stem trial component 14 into engagement with the lobes 96. In that way, the tabs and slots define a secondary retention mechanism that constrains relative rotation between the stem trial component 14 and the reamer 12, thereby avoiding possible detachment of the reamer 12 from the stem trial component 14.

It should be appreciated that in other embodiments the outer sleeve may include additional slots and the surgical reamer may include additional tabs to be received in the additional slots. It should also be appreciated that in other embodiments the reamer may include only a single tab and the outer sleeve a single slot. In still other embodiments, such as, for example, the embodiment described below in regard to FIGS. 6-7, the outer sleeve may include one or more tabs and the surgical reamer may include one or more slots configured to receive the tab(s) of the outer sleeve to constrain the relative rotation between the outer sleeve and the reamer. In still other embodiments, the tabs and slots may be incorporated into a portion of the central rod.

Figure 2:
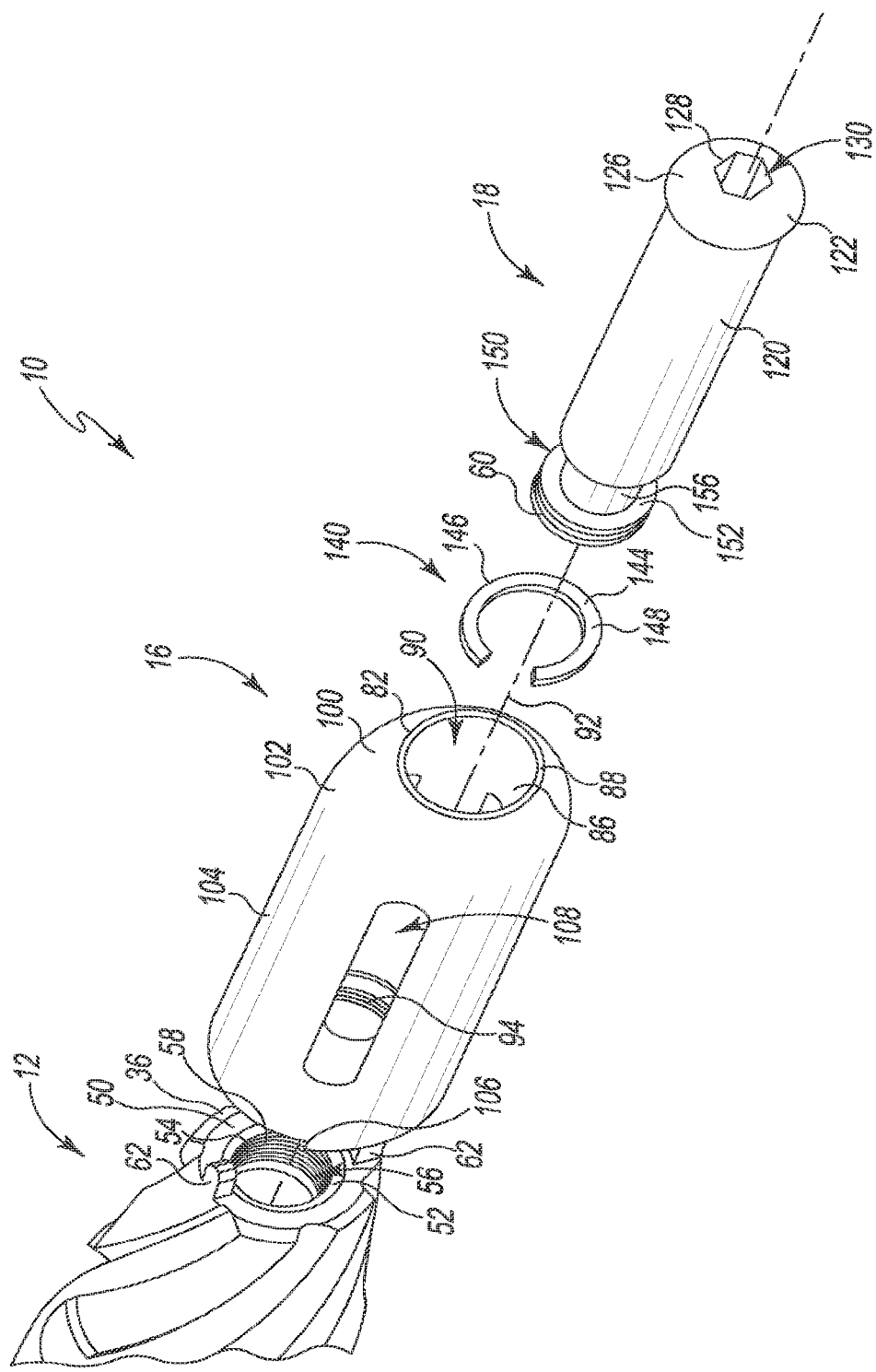
FIG. 2 is another exploded perspective view of the system of FIG. 1.

As shown in FIG. 2, the outer sleeve 16 includes a frustoconical surface 100 extending from the distal end 82 to an edge 102. The outer sleeve 16 includes a cylindrical outer surface 104 that extends from the edge 102 to the proximal end 80. In the illustrative embodiment, each of the slots 68 includes an opening 106 in the outer surface 104. The outer sleeve 16 also includes a number of longitudinal slots 110 that extend through outer surface 104 and the inner wall 86 to open into the passageway 90.

The outer sleeve 16 is illustratively formed from an implant-grade metallic material such as, for example, cobalt chromium or stainless steel. It should be appreciated that in other embodiments the outer sleeve may be formed from a polymeric material such as, for example, polyethylene. In the illustrative embodiment, the outer sleeve is formed as a single monolithic component. In other embodiments, the outer sleeve may be formed from one or more components that are later assembled.

As described above, the stem trial component 14 also includes a central rod 18 that extends through the outer sleeve 16. Returning to FIG. 1, the central rod 18 includes an elongated body 120 sized to be positioned in the passageway 90 of the outer sleeve 16 and a threaded end 60 extending from the elongated body 120. As described above, the threaded end 60 is sized to be positioned in the threaded aperture 56 defined in the surgical reamer 12 to couple the stem trial component 14 to the reamer. It should be appreciated that the threaded end 60 may also engage other surgical instruments such as, for example, a broach, a femoral trial component, or a tibial trial component.

The central rod 18 also includes a distal tip 122 that is attached to the opposite end of the elongated body 120. An annular shoulder wall 124 is defined where the distal tip 122 joins the elongated body 120. When the central rod 18 is attached to the surgical reamer 12, the shoulder wall 124 engages the distal end 82 of the outer sleeve 16 and the proximal end 80 of the sleeve 16 engages the distal end 36 of the reamer shaft 30 such that the outer sleeve 16 is clamped between the distal tip 122 of the central rod 18 and the reamer shaft 30.

As shown in FIG. 2, the distal tip 122 includes a frusto-conical outer surface 126 that extends from the annular shoulder wall 124 to a distal surface 128. In the illustrative embodiment, the distal surface 128 is substantially planar. It should be understood that the term "substantially" refers to a range within typical manufacturing tolerances. As such, a surface that is substantially planar is one that is flat within typical manufacturing tolerances. A socket 130 is defined in the distal surface 128 and is configured to receive a wrench or other tool head to rotate the central rod 18 and thread it onto the surgical reamer 12. A torque wrench may be used to apply a predetermined load to the assembly to secure the stem trial component 14 to the surgical reamer 12. The socket 130 is illustratively hexagonal-shaped to receive a hex-head wrench. It should be appreciated that in other embodiments other socket configurations may be used.

The central rod 18 is illustratively formed from an implant-grade metallic material such as, for example, cobalt chromium or stainless steel. It should be appreciated that in other embodiments the outer sleeve may be formed from a polymeric material such as, for example, polyethylene. In the illustrative embodiment, the central rod is formed as a single monolithic component. In other embodiments, the central rod may be formed from one or more components that are later assembled.

Figure 5:
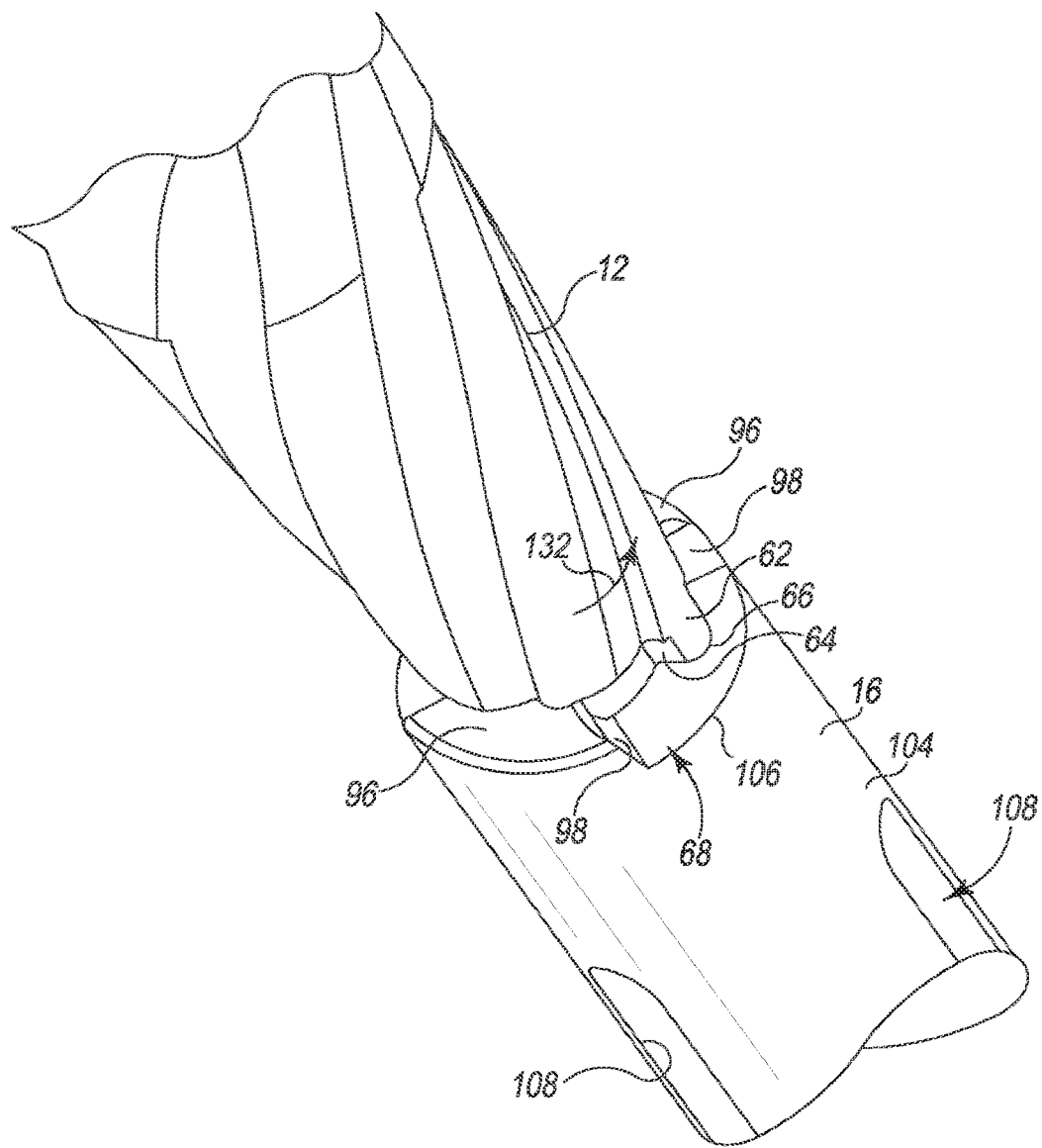
FIG. 5 is a perspective view of a secondary retention mechanism of the system of FIG. 1.

In use, as shown in FIG. 4, the distal tip 122 of the rod 18 cooperates with the outer sleeve 16 to define the outer geometry of the stem trial component 14, which, as described above, is shaped to match the outer geometry of an elongated stem component. The distal tip 122 is positioned adjacent to the distal end 82 of the outer sleeve 16 and the threaded end 60 of the rod 18 is positioned adjacent to the proximal end 80 when the stem trial component 14 is assembled for use as a pilot guide with the reamer or with other surgical instruments. Because the outer sleeve 16 is clamped between the distal tip 122 and the surgical reamer 12, relative rotation between the stem trial component 14 and the reamer 12 is prevented, and the outer sleeve 16 and the rod 18 (i.e., the stem trial component 14) are configured to rotate with the reamer 12 during a cutting step and act as a pilot for the reamer 12. As described above and shown in FIGS. 4-5, the distal tabs 62 of the reamer 12 are positioned in the slots 68 defined in the outer sleeve 16 when the outer sleeve 16 is clamped between the distal tip 122 and the surgical reamer 12. If the threaded connection between the surgical reamer 12 and the central rod 18 loosens during a surgical procedure, rotation of the reamer 12 relative to the outer sleeve 16, which is indicated in FIG. 5 by arrow 132, may advance the distal tabs 62 of the surgical reamer 12 into engagement with the lobes 96, thereby inhibiting further rotation of the reamer 12 relative to the stem trial component 14 and detachment of the component 14 from the reamer 12.

The central rod 18 is configured to slide within the passageway 90 along the longitudinal axis 92 to permit the proximal end of the rod to extend out of (or retract into) the passageway 90. In the illustrative embodiment, the stem trial component 14 also includes a retainer 140 configured to maintain the connection between the outer sleeve 16 and the central rod 18. As shown in FIG. 4, the outer sleeve 16 has an annular groove 142 defined in the inner wall 86, which opens into the passageway 90, and the retainer 140 is positioned in the groove 142. As shown in FIGS. 2 and 4, the retainer 140 is illustratively a ring 144 that has an outer rim 146 positioned in the groove 142 and an inner rim 148 that is positioned in the passageway 90.

The retainer 140 is illustratively formed from an implant-grade metallic material such as, for example, cobalt chromium or stainless steel. It should be appreciated that in other embodiments the outer sleeve may be formed from a polymeric material such as, for example, polyethylene. To assemble the retainer 140 to the outer sleeve 16, the retainer 140 may be clamped to reduce its diameter, and the clamped retainer may be advanced into the passageway 90. When positioned over the groove 142, the retainer 140 may be released to "spring" back into the unclamped configuration shown in FIGS. 2 and 4. In the illustrative embodiment, the retainer is formed as a single monolithic component. In other embodiments, the retainer may be formed from one or more components that are later assembled.

Returning to FIGS. 1-2, the central rod 18 has a pocket 150 defined in the elongated body 120 adjacent to the threaded end 60. The pocket 150 is defined between a pair of end walls 152, 154 and an inner beam 156 of the central rod 18. As shown in FIG. 4, the inner rim 148 of the retainer 140 is positioned in the pocket 150 of the rod 18. The interaction between the retainer 140 and the walls 152, 154 limits the freedom of the rod 18 to slide within the passageway 90.

During a surgical procedure, a surgeon or other user may select a surgical reamer 12 of appropriate size for use with a patient's bone. The surgeon may also select a stem trial component 14 (including an outer sleeve 16 and central rod 18) of appropriate length and diameter. To attach the stem trial component 14 to the selected reamer 12, the user may align the distal end 36 of the reamer 12 with the proximal end 80 of the outer sleeve 16. Initially, the central rod 18 may be bottomed against the retainer 140, with its inner wall 152 engaged with the retainer, its threaded end 60 in the passageway 90, and its distal tip 122 spaced apart from the distal end 82 of the outer sleeve 16. The user may rotate the outer sleeve 16 and/or reamer 12 relative to each other to align the distal tabs 62 of the reamer 12 with the slots 68 defined in the outer sleeve 16. The user may then advance the proximal end 80 of the outer sleeve 16 into contact with the distal end 36 of the reamer 12, thereby positioning the distal tabs 62 of the reamer 12 in the slots 68 defined in the outer sleeve 16.

To secure the stem trial component 14 to the reamer 12, the user may slide the central rod 18 along the passageway 90 of the outer sleeve 16 to place the threaded end 60 into contact with the distal end 36 of the reamer 12. The user may thread the end 60 into the aperture 56 by rotating the central rod 18 about the axis 92 relative to the outer sleeve 16 and the reamer 12. When the shoulder wall 124 of the central rod 18 engages the distal end 82 of the outer sleeve 16, the user may apply a predefined amount of torque to clamp the outer sleeve 16 between the shoulder wall 124 of the central rod 18 and the reamer distal end 36.

Figure 6:
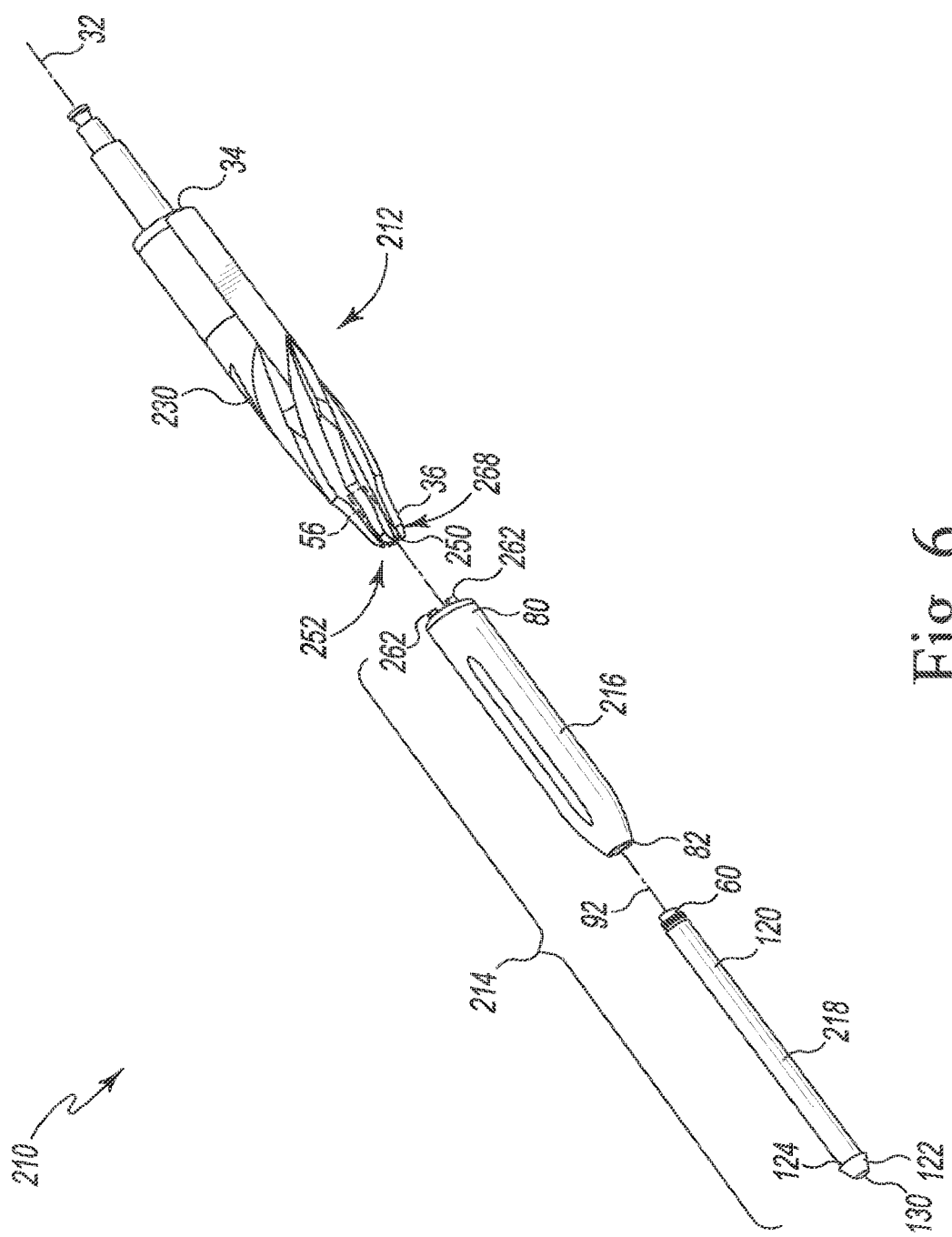
FIG. 6 is an exploded perspective view of another embodiment of an orthopaedic surgical instrument system.
Figure 7:
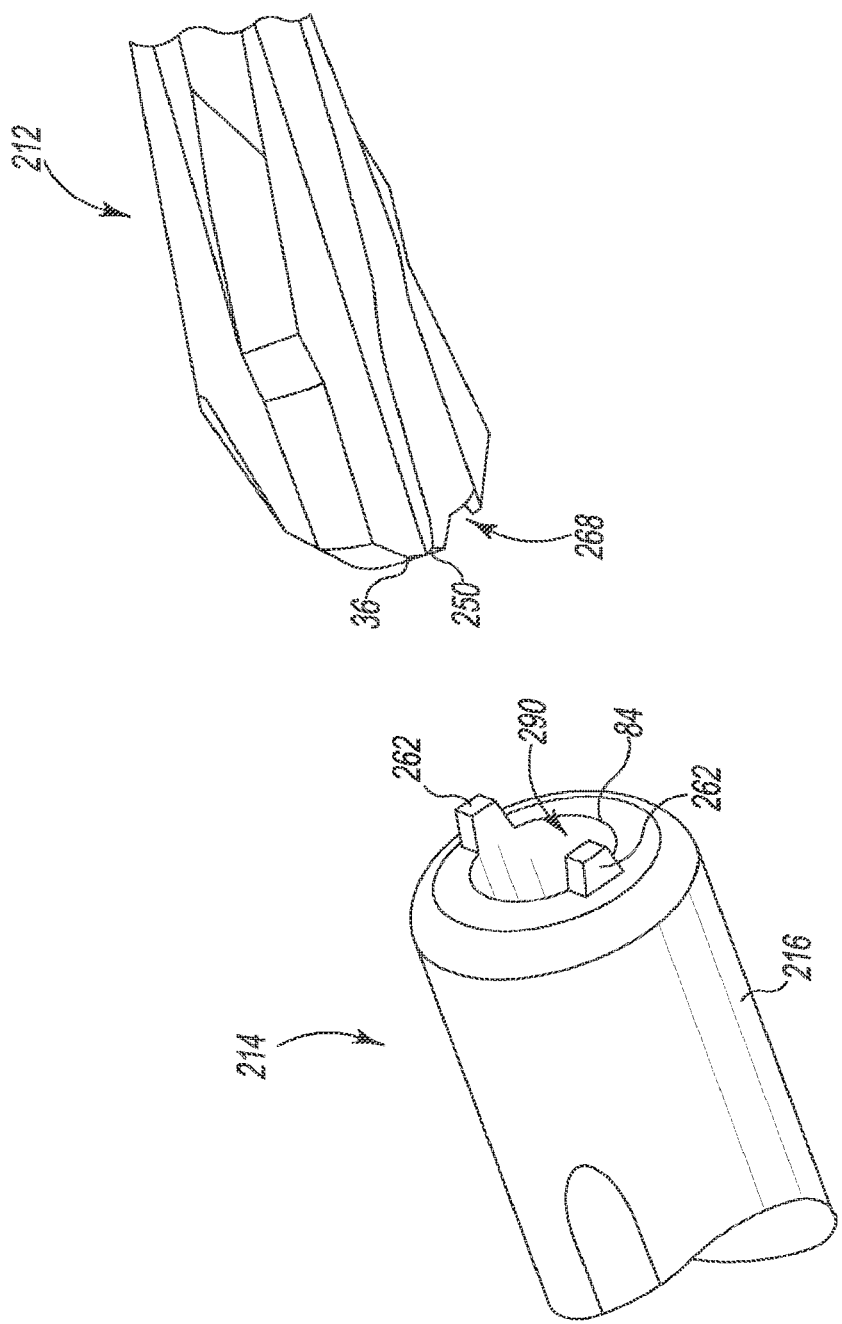
FIG. 7 is a perspective view of a distal end of the surgical reamer and a proximal end of a stem trial component of the system of FIG. 6.

Referring now to FIGS. 6-7, another embodiment of an orthopaedic surgical instrument system (hereinafter system 210) is shown. Many of the features of the embodiment of FIGS. 6-7 are the same or similar to the features described above in regard to FIGS. 1-5. The same reference numbers will be used to identify such features in the system 210. The system 210, like the system 10, includes a surgical reamer 212 that is configured to be attached to a stem trial component 214. The stem trial component 214 includes an outer sleeve 216 and a central rod 218.

The surgical reamer 212 includes a shaft 230 that extends along a longitudinal axis 32 from a proximal end 34 to a distal end 36. The distal end 36 of the reamer shaft 230 includes an annular rim wall 250 that surrounds an opening 252. A pair of slots 268 are defined in the annular rim wall 250. Similar to the slots 68 described above in regard to FIGS. 1-5, the slots 268 are sized to receive tabs 262 extending from the stem trial component 214 to inhibit relative rotation between the reamer 212 and the stem trial component 214. In other words, the arrangement of the tabs and slots on the stem trial component and the reamer in the system 210 are reversed from those shown and described in regard to system 10. It should be appreciated that in still to other embodiments the reamer may include one tab and one slot, while the stem trial component includes a corresponding one slot and one tab.

As shown in FIGS. 6-7, the tabs 262 extend from the proximal end 80 of the outer sleeve 216 of the stem trial component 14. The tabs 262 are arranged circumferentially around the opening 84 of the passageway 90 extending through the outer sleeve 216.

As described above, the stem trial component 214 also includes a central rod 218 that extends through the outer sleeve 216. Returning to FIG. 6, the central rod 218 includes an elongated body 120 sized to be positioned in the passageway 90 of the outer sleeve 216 and a threaded end 60 extending from the elongated body 120. The threaded end 60 is sized to be positioned in the threaded aperture 56 defined in the surgical reamer 12.

The central rod 218 also includes a distal tip 122 that is attached to the opposite end of the elongated body 120. An annular shoulder wall 124 is defined where the distal tip 122 joins the elongated body 120. When the central rod 218 is attached to the surgical reamer 212, the shoulder wall 124 engages the distal end 82 of the outer sleeve 16 and the proximal end 80 of the sleeve 216 engages the distal end 36 of the reamer shaft 230 such that the outer sleeve 216 is clamped between the distal tip 122 of the central rod 218 and the reamer shaft 230 in a manner similar to that described above in regard to FIGS. 1-5.

The central rod 218 is configured to slide within the passageway 90 along the longitudinal axis 92. In contrast to the rod 18 of FIGS. 1-5, the central rod 218 may be decoupled from the outer sleeve 216. In that way, the central rod 218 may be used with outer sleeves of different sizes, including, for example, sleeves having different diameters.

Figure 8:
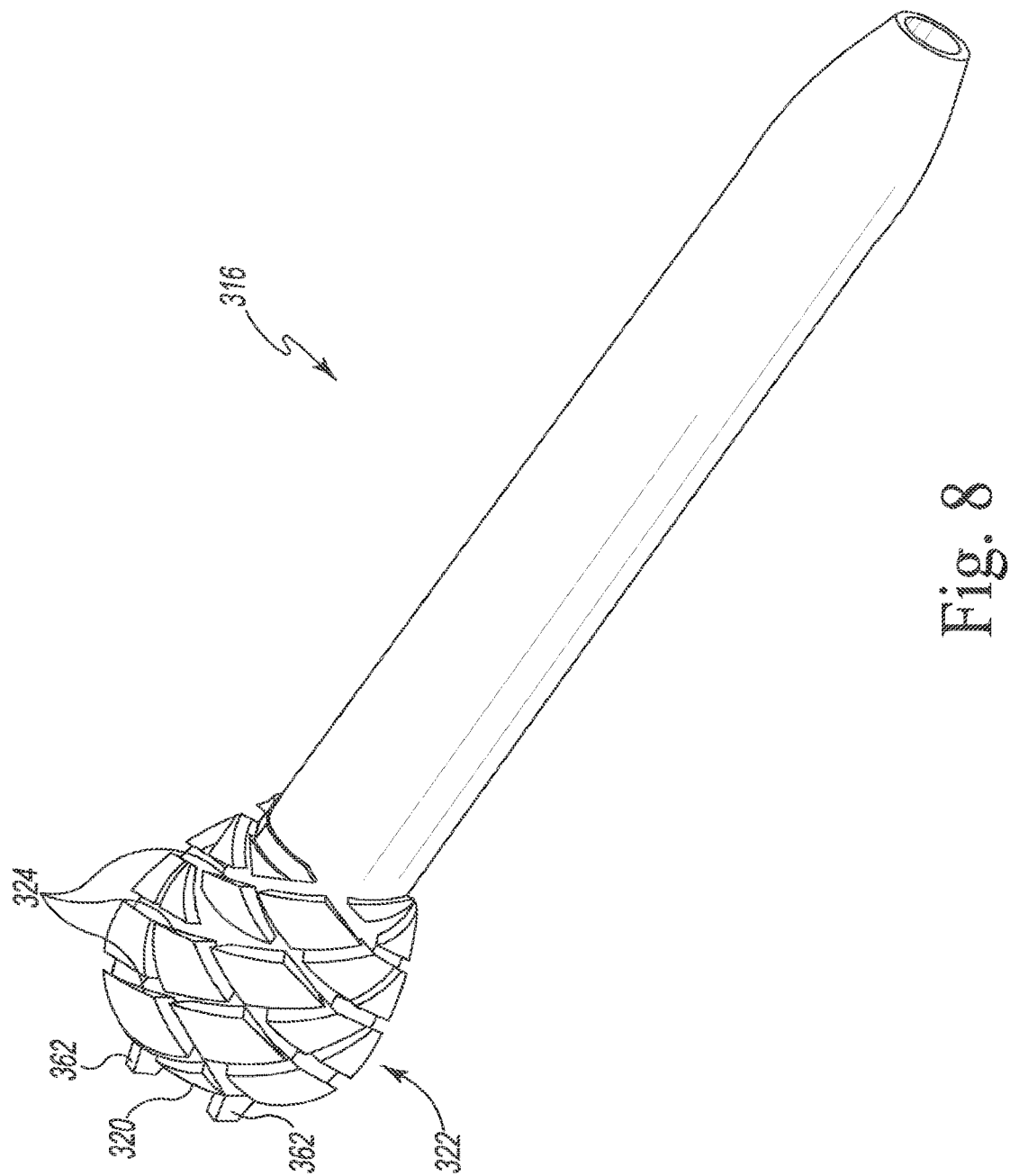
FIG. 8 is a perspective view of another embodiment of a stem trial component.

Referring now to FIG. 8, the outer sleeve of the stem trial component 214 may be replaced with an outer sleeve 316. Like the outer sleeve 216, a pair of tabs 362 extend from a proximal end 320 of the outer sleeve 316 of the stem trial component 14. The tabs 362 are arranged circumferentially around the opening 84 of the passageway 90 extending through the outer sleeve 316 and are configured to be received in the slots 268 of the reamer.

The outer sleeve 316 also includes a rasp 322 that is positioned on the proximal end 320. The rasp 322 includes a plurality of cutting teeth 324 that define a cup or cupule-shaped outer surface extending around the outer perimeter of the sleeve end 320. The rasp 322 is configured to cut the bone in both a rotational and linear/longitudinal direction. It should be appreciated that a similar rasp may be included on the outer sleeve 16 described above in regard to FIGS. 1-5.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of assembling an orthopaedic surgical instrument, the method comprising:
   selecting a surgical reamer for use in resecting a portion of a patient's bone,
   aligning an outer sleeve of a stem trial component with a distal end of a shaft of the surgical reamer,
   advancing the outer sleeve into engagement with the distal end of the reamer shaft,
   advancing a central rod of the stem trial component along a passageway defined in the outer sleeve into engagement with the distal end of the reamer shaft, and
   threading the central rod into the distal end of the reamer shaft to couple the stem trial component to the surgical reamer for use in resecting the portion of the patient's bone.

2. The method of claim 1, wherein advancing the outer sleeve into engagement with the distal end of the reamer shaft comprises positioning a distal tab extending from the distal end of the reamer shaft into a slot defined in the outer sleeve to constrain relative rotational movement between the outer sleeve and the surgical reamer.

3. The method of claim 2, wherein threading the central rod into the distal end of the reamer shaft includes threading the central rod into the distal end of the reamer shaft while the distal tab of the surgical reamer is received in the slot defined in the outer sleeve of the stem trial component.

4. The method of claim 1, wherein threading the central rod into the distal end of the reamer shaft includes clamping the outer sleeve between an annular shoulder wall of the central rod and the distal end of the shaft of the surgical reamer to prevent relative rotational movement between the stem trial component and the surgical reamer.

* * * * *